United States Patent
Li et al.

(10) Patent No.: US 8,725,258 B2
(45) Date of Patent: May 13, 2014

(54) METHOD AND APPARATUS FOR AUTOMATED ADJUSTMENT OF ARRHYTHMIA DETECTION DURATION

(75) Inventors: Dan Li, Shoreview, MN (US); Shelley Cazares, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1613 days.

(21) Appl. No.: 11/467,421

(22) Filed: Aug. 25, 2006

(65) Prior Publication Data

US 2008/0051843 A1    Feb. 28, 2008

(51) Int. Cl.
*A61N 1/362*    (2006.01)

(52) U.S. Cl.
CPC .................................. *A61N 1/3624* (2013.01)
USPC .............................................. 607/14; 600/518

(58) Field of Classification Search
USPC ............... 607/2, 4, 6, 7, 9, 11, 14, 17, 22, 24; 600/515, 518, 519, 526
See application file for complete search history.

(56) References Cited

U.S. PATENT DOCUMENTS

| | | | |
|---|---|---|---|
| 5,063,928 A | 11/1991 | Grevis et al. | |
| 5,978,707 A | 11/1999 | Krig et al. | |
| 6,151,524 A | 11/2000 | Krig et al. | |
| 6,317,632 B1 | 11/2001 | Krig et al. | |
| 6,400,982 B2 * | 6/2002 | Sweeney et al. | 600/515 |
| 6,522,925 B1 | 2/2003 | Gilkerson et al. | |
| 6,636,764 B1 | 10/2003 | Fain et al. | |
| 6,842,644 B2 | 1/2005 | Anderson et al. | |
| 6,873,870 B2 * | 3/2005 | Ferek-Petric | 600/518 |
| 7,010,344 B2 | 3/2006 | Burnes et al. | |
| 7,027,856 B2 | 4/2006 | Zhou et al. | |
| 7,076,298 B2 | 7/2006 | Padmanabhan et al. | |
| 2004/0162497 A1 * | 8/2004 | Bennett et al. | 600/513 |
| 2005/0107838 A1 * | 5/2005 | Lovett et al. | 607/17 |
| 2005/0149135 A1 * | 7/2005 | Krig et al. | 607/14 |
| 2005/0149143 A1 * | 7/2005 | Libbus et al. | 607/44 |
| 2005/0222629 A1 * | 10/2005 | Perschbacher et al. | 607/4 |
| 2005/0256550 A1 | 11/2005 | Gilkerson et al. | |
| 2006/0095083 A1 * | 5/2006 | Zhang et al. | 607/14 |

OTHER PUBLICATIONS

Brugada, J., et al., "Enhanced detection criteria in implantable defibrillators.", *J Cardiovasc Electrophysiol.*, 9(3), (Mar. 1998), 261-8.

Brugada, J., "Is inappropriate therapy a resolved issue with current implantable cardioverter defibrillators?", *Am J Cardiol.*, 83(5B), (Mar. 11, 1999), 40D-44D.

(Continued)

*Primary Examiner* — Kennedy Schaetzle
*Assistant Examiner* — Erica Lee
(74) *Attorney, Agent, or Firm* — Schwegman Lundberg & Woessner, P.A.

(57) ABSTRACT

A cardiac rhythm management (CRM) system delivers anti-tachyarrhythmia therapies and uses patient-specific and/or tachyarrhythmia event-specific information to automatically set and adjust one or more arrhythmia detection durations. In one embodiment, the CRM system initializes and updates the one or more arrhythmia detection durations using patient-specific information such as medical history and recent medical trends. In another embodiment, the CRM dynamically adjusts the one or more arrhythmia detection durations using the patient's hemodynamic performance. One example of such an arrhythmia detection duration is a sustained rate duration (SRD) that starts when a tachyarrhythmia such as a supraventricular tachyarrhythmia is detected. An anti-tachyarrhythmia therapy is delivered only if the tachyarrhythmia sustains throughout the SRD.

34 Claims, 8 Drawing Sheets

(56) References Cited

OTHER PUBLICATIONS

Cates, Adam W., et al., "Method and Apparatus for Indication-Based Programming of Cardiac Rhythm Management Devices", U.S. Appl. No. 11/110,500, filed Apr. 20, 2005, 32 Pages.

Dorian, P., et al., "Randomized controlled study of detection enhancements versus rate-only detection to prevent inappropriate therapy in a dual-chamber implantable cardioverter-defibrillator", *Heart Rhythm*, 1(5), (Nov. 2004), 540-7.

Li, Dan, et al., "Method and Apparatus for Controlling Anti-Tachyarrhythmia Pacing Using Hemodynamic Sensor", U.S. Appl. No. 11/312,082, filed Dec. 20, 2005, 49 Pages.

Li, Dan, et al., "Method and Apparatus for Morphology-Based Arrhythmia Classification Using Cardiac and Other Physiological Signals", U.S. Appl. No. 11/316,332, filed Dec. 22, 2005, 63 Pages.

\* cited by examiner

METHOD AND APPARATUS FOR AUTOMATED ADJUSTMENT OF ARRHYTHMIA DETECTION DURATION

TECHNICAL FIELD

This document relates generally to cardiac rhythm management (CRM) systems and particularly to an anti-tachyarrhythmia system that automatically adjusts one or more arrhythmia detection durations using patent-specific and/or tachyarrhythmia event-specific information.

BACKGROUND

Tachyarrhythmias are abnormal heart rhythms characterized by a rapid heart rate. Tachyarrhythmias generally include supraventricular tachyarrhythmia (SVT, including atrial tachyarrhythmia, AT) and ventricular tachyarrhythmia (VT). Fibrillation is a form of tachyarrhythmia further characterized by an irregular heart rhythm. In a normal heart, the sinoatrial node, the heart's predominant natural pacemaker, generates electrical impulses, called action potentials, that propagate through an electrical conduction system to the atria and then to the ventricles of the heart to excite the myocardial tissues. The atria and ventricles contract in the normal atrioventricular sequence and synchrony to result in efficient blood-pumping functions indicated by a normal hemodynamic performance. VT occurs when the electrical impulses propagate along a pathologically formed self-sustaining conductive loop within the ventricles or when a natural pacemaker in a ventricle usurps control of the heart rate from the sinoatrial node. When the atria and the ventricles become dissociated during VT, the ventricles may contract before they are properly filled with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Cardioversion and defibrillation are used to terminate most tachyarrhythmias, including AT, VT, and VF. An implantable cardioverter/defibrillator (ICD) is a cardiac rhythm management (CRM) device that delivers an electric shock to terminate a detected tachyarrhythmia episode by depolarizing the entire myocardium simultaneously and rendering it refractory. Another type of electrical therapy for tachyarrhythtnia is anti-tachyarrhythmia pacing (ATP). In ATP, the heart is competitively paced in an effort to interrupt the reentrant loop causing the tachyarrhythmia. An exemplary ICD includes ATP and defibrillation capabilities so that ATP is delivered to the heart when a non-fibrillation VT is detected, while a defibrillation shock is delivered when VF occurs.

The efficacy of cardioversion, defibrillation, and ATP in terminating tachyarrhythmia depends on the type and origin of the tachyarrhythmia. An unnecessary therapy delivered during a non-life-threatening tachyarrhythmia episode may cause substantial pain in the patient and reduces the longevity of the ICD while providing the patient with little or no benefit. On the other hand, a necessary therapy withheld during a life-threatening tachyarrhythmia episode may result in irreversible harm, including death. For these and other reasons, there is a need for detecting tachyarrhythmia in a way that ensures patient safety while reducing unnecessary delivery of therapy.

SUMMARY

A CRM system delivers anti-tachyarrhythmia therapies and uses patient-specific and/or tachyarrhythmia event-specific information to automatically set and adjust one or more arrhythmia detection durations. In one embodiment, the CRM system initializes and updates the one or more arrhythmia detection durations using patient-specific information such as medical history and recent medical trends. In another embodiment, the CRM dynamically adjusts the one or more arrhythmia detection durations using the patient's hemodynamic performance. One example of such an arrhythmia detection duration is a sustained rate duration (SRD) that starts when a tachyarrhythmia such as an SVT is detected. An anti-tachyarrhythmia therapy is delivered only if the detected SVT sustains throughout the SRD.

In one embodiment, a CRM system includes a tachyarrhythmia detector and a duration controller. The tachyarrhythmia detector detects a tachyarrhythmia during an arrhythmia detection duration. The duration controller includes a duration timer and a duration adjuster. The duration timer times the arrhythmia detection duration. The duration adjuster includes one or more of a duration initialization module and a dynamic duration adjustment module. The duration initialization module automatically determines an initial value using one or more indication parameters related to an indication for an anti-tachyarrhythmia therapy and sets a base value of the arrhythmia detection duration to the initial value. The dynamic duration adjustment module dynamically adjusts the arrhythmia detection duration using a signal indicative of hemodynamic performance.

In one embodiment, a method for operating a CRM system is provided. An arrhythmia detection duration is timed. A tachyarrhythmia is detected during the arrhythmia detection duration. The arrhythmia detection duration is adjusted automatically using one or more indication parameters related to an indication for an anti-tachyarrhythmia therapy and/or adjusted dynamically using a signal indicative of hemodynamic performance.

In one embodiment, a CRM system includes a tachyarrhythmia detector, a therapy output circuit, a therapy controller, and a duration controller. The tachyarrhythmia detector determines whether a tachyarrhythmia sustains during a sustained rate duration (SRD). The therapy output circuit delivers an anti-tachyarrhythmia therapy. The therapy controller initiates a delivery of the anti-tachyarrhythmia therapy in response to an expiration of the SRD and withholds the delivery of the anti-tachyarrhythmia therapy if the SRD is terminated before the expiration. The duration controller includes a duration timer and a duration adjuster. The duration timer times the SRD. The duration adjuster receives a sensed physiologic signal and/or stored patient-specific information, and automatically adjusts the SRD using the sensed physiologic signal and/or the stored patient-specific information.

In one embodiment, a method for operating a CRM system is provided. A sensed physiologic signal and/or stored patient-specific information are received. An SRD is automatically adjusted using the sensed physiologic signal and/or the stored patient-specific information. Whether a tachyarrhythmia sustains is determined during the SRD. A delivery of an anti-tachyarrhythmia therapy is initiated in response to an expiration of the SRD. The delivery of the anti-tachyarrhythmia therapy is withheld if the SRD is terminated before expiring.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
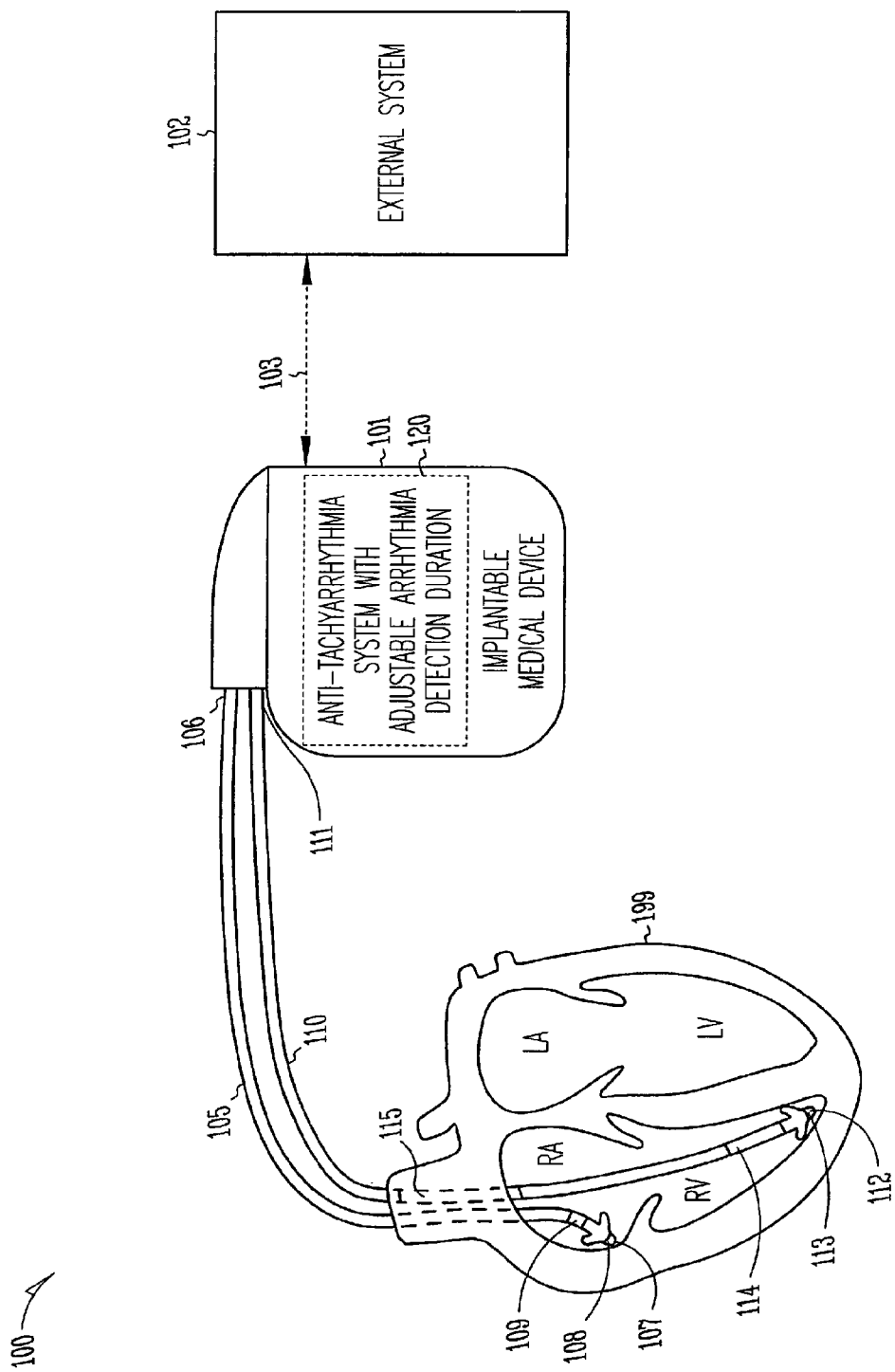
FIG. 1 is an illustration of an embodiment of a CRM system including an anti-tachyarrhythmia system with adjustable arrhythmia detection duration and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

The relationship between a heart rate and a cardiac cycle length (also known as cardiac interval), as used in this document, is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, if a tachyarrhythmia is detected when the ventricular rate exceeds a tachyarrhythmia threshold rate, an equivalent process is to detect the tachyarrhythmia when the ventricular cycle length (also known as ventricular interval) falls below a tachyarrhythmia threshold interval. The appended claims should be construed to cover such variations.

In this document, a "fast beat" refers to a heart beat having a heart rate that falls into a tachyarrhythmia detection zone, which is typically defined by at least one tachyarrhythmia detection threshold, and a "slow beat" refers to a heart beat having a heart rate that is below the tachyarrhythmia detection zone. In other words, a "fast beat" is a heart beat having a tachyarrhythmic heart rate, and a "slow beat" is a heart beat having a heart rate that is not tachyarrhythmic. A paced heart beat is typically considered as a slow beat.

This document discusses a CRM system that delivers anti-tachyarrhythmia therapies and uses patient-specific and/or tachyarrhythmia event-specific information to automatically set and adjust one or more arrhythmia detection durations. In one embodiment, the system initializes and updates the one or more arrhythmia detection durations for a patient using the patient's medical record including information such as medical history and recent medical trends. In another embodiment, the system dynamically adjusts the one or more arrhythmia detection durations using the patient's hemodynamic performance sensed during a tachyarrhythmia episode. The one or more arrhythmia detection durations include one or more durations within which an arrhythmia is detected, verified, classified, or otherwise analyzed, as illustrated by the following example.

In one example of an ICD that delivers ventricular cardioversion/defibrillation pulses, a detection of three consecutive fast beats from a ventricular electrogram starts a tachyarrhythmia detection and classification process. In response to the detection of three consecutive fast beats, a tachyarrhythmia detection window is started. The tachyarrhythmia detection window includes ten consecutively detected heart beats starting with and including the three consecutive fast beats. If at least eight out of the ten heart beats in the tachyarrhythmia detection window are fast beats (i.e., the tachyarrhythmia detection window is satisfied), a tachyarrhythmia verification duration is started. Otherwise, the tachyarrhythmia detection and classification process is terminated without delivering a ventricular anti-tachyarrhythmia therapy.

During the tachyarrhythmia verification duration, a moving verification window of ten consecutively detected heart beats is used to determine whether the detected tachyarrhythmia sustains. If at least six out of the ten heart beats in the verification window are fast beats (i.e., the verification window is satisfied), the detected tachyarrhythmia is considered to be sustaining. If this verification window fails to be satisfied at any time during the tachyarrhythmia verification duration, the tachyarrhythmia detection and classification process is terminated without delivering a ventricular anti-tachyarrhythmia therapy. If the detected tachyarrhythmia episode is determined to be sustaining throughout the tachyarrhythmia verification duration, it is classified by its origin and/or type to determine whether a ventricular anti-tachyarrhythmia therapy will be necessary.

If the detected tachyarrhythmia episode is classified as a type of tachyarrhythmia for which a ventricular cardioversion/defibrillation therapy is to be delivered, such as a VT episode, the preparation for the ventricular cardioversion/defibrillation therapy is started. After the preparation is completed, a tachyarrhythmia reconfirmation window of three consecutive heart beats is started, immediately before a scheduled ventricular cardioversion/defibrillation pulse delivery. If at least two out of the three heart beats in the tachyarrhythmia reconfirmation window are fast beats (i.e., the tachyarrhythmia reconfirmation window is satisfied), the detected tachyarrhythmia is considered to be still sustaining, and the ventricular cardioversion/defibrillation pulse is delivered.

If the detected tachyarrhythmia episode is classified as a type of tachyarrhythmia for which no ventricular anti-tachyarrhythmia therapy is needed, such as an SVT episode, a sustained rate duration (SRD), also similarly referred to in the art as High Rate Timeout™ (Medtronic, Inc.) and Maximum Time to Diagnosis™ (St. Jude Medical, Inc.), is started. During the SRD, the heart rate is monitored to determine whether the tachyarrhythmia episode sustains. If the tachyarrhythmia episode sustains throughout the SRD, the ventricular anti-tachyarrhythmia therapy is delivered when the SRD expires even though the detected tachyarrhythmia episode is classified as an SVT episode. The tachyarrhythmia episode sustains if the heart rate remains within a predetermined tachyarrhythmia rate detection zone (such as a VT rate detection zone). In one embodiment, the tachyarrhythmia episode is considered sustaining when an average heart rate (such as an average of heart rates detected within a moving window) falls within the predetermined tachyarrhythmia rate detection zone. In another embodiment, the tachyarrhythmia episode is considered sustaining when a predetermined majority of heart beats within a moving detection window are fast beats, such as when at least six out of ten heart beats are fast beats. In one embodiment, the SRD is programmable between 10 seconds and 60 minutes, with approximately three minutes as a specific example. The SRD is applied to determine whether a detected tachyarrhythmia needs to be treated because of a sustaining high heart rate, after the tachyarrhythmia is classified to be a type that is not to be treated. Thus, the SRD functions as a "safety net" capable of overriding a tachyarrhythmia classification to deliver a therapy. The length of the SRD should reflect a balanced consideration between prompt treatment for a potentially life-threatening tachyarrhythmia and avoidance of an unnecessary yet painful treatment. While the SRD may be programmable by a user such as a physician or other caregiver, the optimization of its value is typically difficult to perform manually before programming the ICD for each individual patient.

As illustrated in the example above, an "arrhythmia detection duration" as used in this document includes any duration within which an arrhythmia is detected, verified, classified, or otherwise analyzed. In various embodiments, such arrhythmia detection durations are specified by a time interval or by number of heart beats. Examples of such an arrhythmia detection duration include the tachyarrhythmia detection window, the tachyarrhythmia verification duration, the verification window, the tachyarrhythmia reconfirmation window, and the SRD. The SRD is specifically discussed below as an example of the arrhythmia detection duration in the present system. Generally, the SRD is substantially longer than many other arrhythmia detection durations, and therefore the automatic adjustment of its length has more significant impact in the overall performance of the ICD.

FIG. 1 is an illustration of one embodiment of a CRM system 100 and portions of the environent in which CRM system 100 operates. CRM system 100 includes an implantable medical device 101 that is electrically coupled to a heart 199 through leads 105 and 110. An external system 102 communicates with implantable medical device 101 via a telemetry link 103.

Implantable medical device 101 delivers anti-tachyarrhythmia therapies such as ATP and cardioversion/defibrillation therapies. In one embodiment, implantable medical device 101 is an implantable cardioverter/defibrillator (ICD) with cardiac pacing capabilities. In another embodiment, in addition to a pacemaker and a cardioverter/defibrillator, implantable medical device 101 further includes one or more of other monitoring and/or therapeutic devices such as a neural stimulator, a drug delivery device, and a biological therapy device. Implantable medical device 101 includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is a pacing lead that includes a proximal end 106 connected to implantable medical device 101 and a distal end 107 placed in the right atrium (RA) of heart 199. A pacing-sensing electrode 108 is located at distal end 107. Another pacing-sensing electrode 109 is located near distal end 107. Electrodes 108 and 109 are electronically connected to implantable medical device 101 via separate conductors in lead 105 to allow sensing of the atrial electrogram and/or delivery of atrial pacing pulses. Lead 110 is a defibrillation lead that includes a proximal end 111 connected to implantable medical device 101 and a distal end 112 placed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to implantable medical device 101 via separate conductors in lead 110. Electrode 113 allows sensing of the ventricular electrogram and/or delivery of ventricular pacing pulses. Electrodes 114 and 115 allow delivery of ventricular cardioversion/defibrillation pulses.

CRM system 100 includes an anti-tachyarrthythmia system 120 that uses at least one adjustable arrhythmia detection duration such as the SRD. The adjustable arrhythmia detection duration has a base value that is initialized to a value determined based on a patient's medical history including one or more indication parameters related to an indication for the anti-tachyarrhythmia therapy. Such indication parameters include patient demographics that indicate the likeliness that a cardiac condition detected from the patient is related to a tachyarrhythmia episode that requires the anti-tachyarrhythmia therapy. The base value is updated based on one or more trend parameters related to a recent trend of one of the patient's medical conditions. When being timed for tachyarrhythmia detection, the arrhythmia detection duration is dynamically adjusted using a sensed signal indicative of the patient's hemodynamic performance. In one embodiment, as illustrated in FIG. 1, anti-tachyarrhythmia system 120 is within implantable medical device 101. In another embodiment, anti-tachyarrhythmia system 120 is distributed in both implantable medical device 101 and external system 102. For example, the value of the arrhythmia detection duration may be initialized in external system 102, but updated and dynamically adjusted by implantable medical device 101. In another example, the base value of the arrhythmia detection duration is initialized and updated in external system 102 and programmed into implantable medical device 101. When being timed for tachyarrhythmia detection, the arrhythmia detection duration is dynamically adjusted in implantable medical device 101.

External system 102 allows for programming of implantable medical device 101 and receives signals acquired by implantable medical device 101. In one embodiment, external system 102 includes a programmer. In another embodiment, external system 102 is a patient management system including an external device in proximity of implantable medical device 101, a remote device in a relatively distant location, and a telecommunication network linking the external device and the remote device. The patient management system allows access to implantable medical device 101 from a remote location, such as for monitoring patient status, adjusting therapies, and obtaining patient's medical records stored in a remote location. Telemetry link 103 is a wireless communication link providing for bidirectional data transmission between implantable medical device 101 and external system 102. In one embodiment, telemetry link 103 is an inductive telemetry link. In an alternative embodiment, telemetry link 103 is a far-field radio-frequency telemetry link. Telemetry link 103 provides for data transmission from implantable medical device 101 to external system 102. This may include, for example, transmitting real-time physiological data acquired by implantable medical device 101, extracting physiological data acquired by and stored in implantable medical device 101, extracting therapy history data stored in implantable medical device 101, and extracting data indicating an operational status of implantable medical device 101 (e.g., battery status and lead impedance). Telemetry link 103 also provides for data transmission from external system 102 to implantable medical device 101. This may include, for example, programming implantable medical device 101 to acquire physiological data, programming implantable medical device 101 to perform at least one self-diagnostic test (such as for a device operational status), programming implantable medical device 101 to enable an available monitoring or therapeutic function, and programming implantable medical device 101 to adjust therapeutic parameters such as pacing and/or cardioversion/defibrillation parameters.

Anti-tachyarrhythmia system 120 may be implemented using a combination of hardware and software. In various embodiments, each element of anti-tachyarrhythmia system 120, including its specific embodiments, may be implemented using an application-specific circuit constructed to perform one or more particular functions or a general-purpose circuit programmed to perform such function(s). Such a general-purpose circuit includes, but is not limited to, a microprocessor or portions thereof, a microcontroller or portions thereof, and a programmable logic circuit or portions thereof For example, a "timer" includes, among other things, an electronic circuit timer constructed to perform the only function of timing a specified duration or a portion of a general-purpose circuit driven by a code instructing that portion of the general-purpose circuit to perform the timing of the specified duration.

Figure 2:
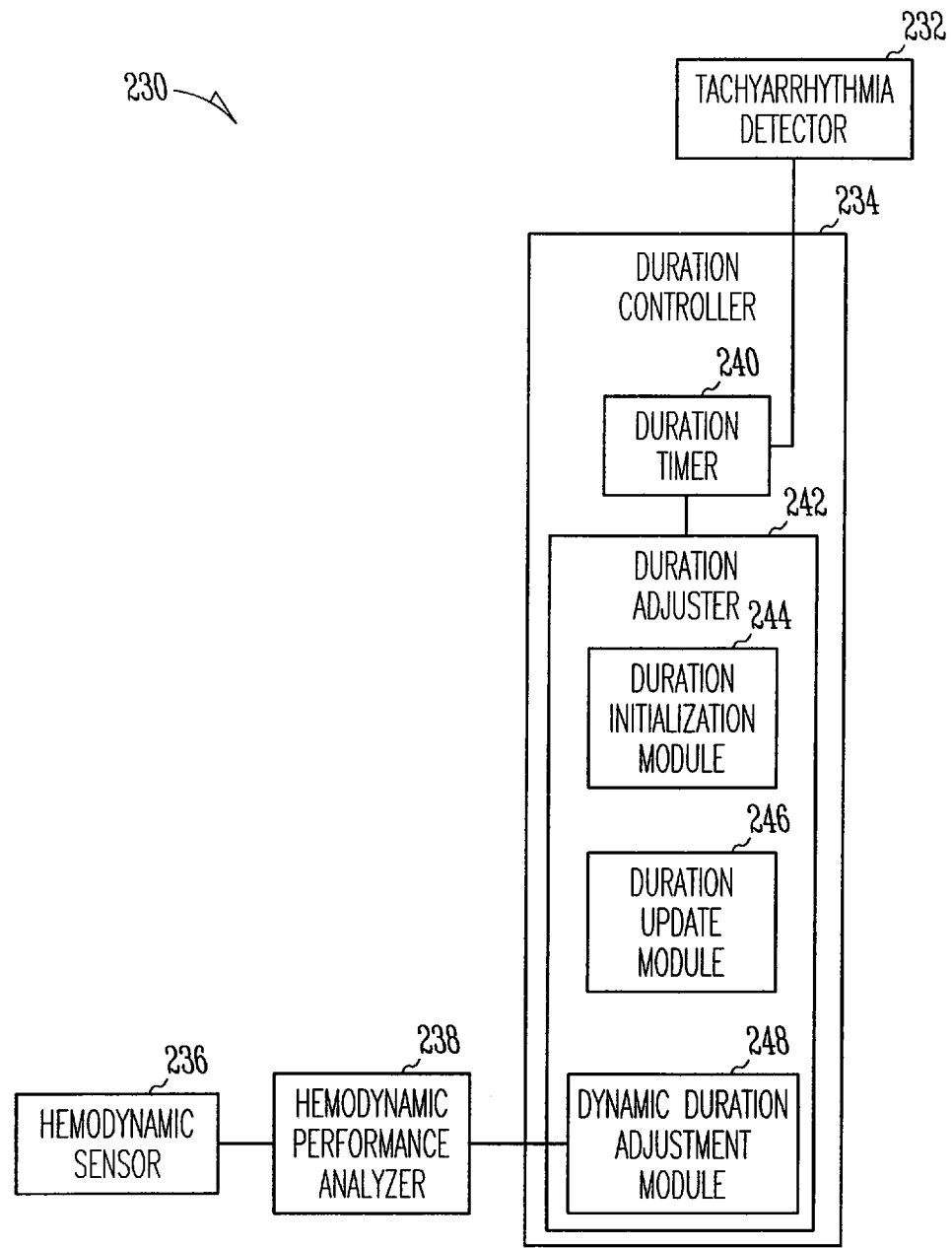
FIG. 2 is a block diagram illustrating an embodiment of an tachyarrhythmia detection system of the anti-tachyarrhythmia system.

FIG. 2 is a block diagram illustrating an embodiment of a tachyarrhythmia detection system 230, which is part of anti-tachyarrhythmia system 120. Tachyarrhythmia detection system 230 includes a tachyarrhythmia detector 232, a duration controller 234, a hemodynamic sensor 236, and a hemodynamic performance analyzer 238. Tachyarrhythmia detector 232 detects a tachyarrhythmia during an arrhythmia detection duration. Duration controller 234 includes a duration timer 240 and a duration adjuster 242. Duration timer 240 times the arrhythmia detection duration. Duration adjuster 242 adjusts the arrhythmia detection duration.

In one embodiment, as illustrated in FIG. 2, duration adjuster 242 includes a duration initialization module 244, a duration update module 246, and a dynamic duration adjustment module 248. In other embodiments, duration adjuster 242 includes any one or more of duration initialization module 244, duration update module 246, and dynamic duration adjustment module 248. Duration initialization module 244 determines an initial value using one or more indication parameters related to an indication for the anti-tachyarrhythmia therapy and sets a base value of the arrhythmia detection duration to the initial value. Duration update module 246 determines an updated value using one or more trend parameters related to a recent trend of a medical condition and sets the base value of the arrhythmia detection duration to the updated value. Dynamic duration adjustment module 248 dynamically adjusts the arrhythmia detection duration using a signal indicative of hemodynamic performance while tachyarrhythmia is being detected during the arrhythmia detection duration. Hemodynamic sensor 236 senses the signal indicative of hemodynamic performance. In one embodiment, hemodynamic performance analyzer 238 produces a hemodynamic stability parameter, and dynamic duration adjustment module 248 computes an adjusted value of the arrhythmia detection duration as a function of the hemodynamic stability parameter and the current value of the arrhythmia detection duration and sets the arrhythmia detection duration to the adjusted value.

As part of anti-tachyarrhythmia system 120, tachyarrhythmia detection system 230 is within implantable medical device 101 in one embodiment, and is distributed in implantable medical device 101 and external system 102 in other embodiments. How tachyarrhythmia detection system 230 is distributed depends on, for example, the overall functions of implantable medical device 101 and external 102 and how frequently the patient is examined by a physician or other caregiver. In one embodiment, duration initialization module 244 is in external system 102, and duration update module 246 and dynamic duration adjustment module 248 are in implantable medical device 101. In another embodiment, duration initialization module 244 and duration update module 246 are in external system 102, and dynamic duration adjustment module 248 is in implantable medical device 101.

Figure 3:
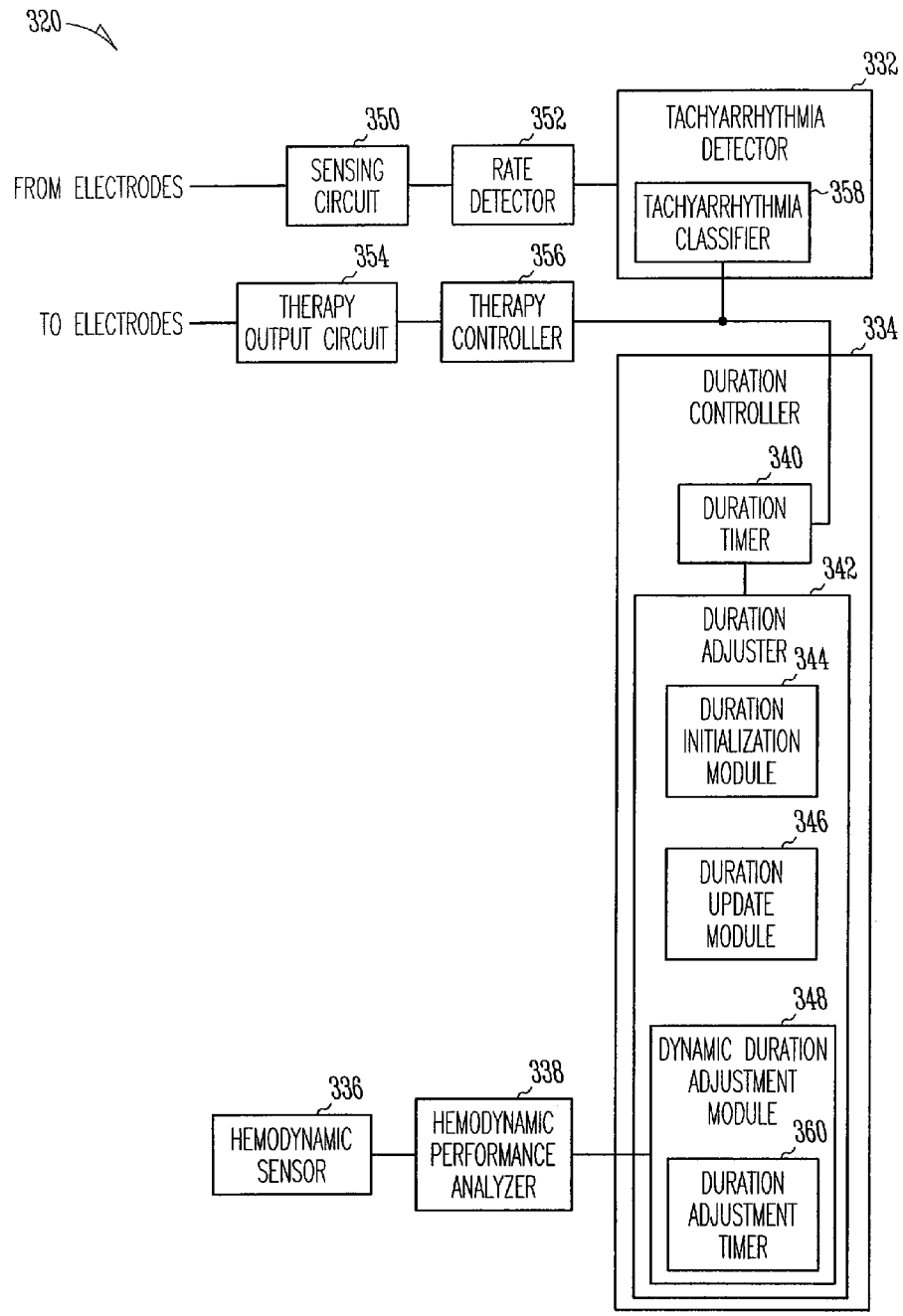
FIG. 3 is a block diagram illustrating an embodiment of the anti-tachyarrhythimia system.

FIG. 3 is a block diagram illustrating an embodiment of an anti-tachyarrhythmia system 320. Anti-tachyarrhythmia system 320 is an embodiment of anti-tachyarrhythmia system 120 and includes a sensing circuit 350, a rate detector 352, a tachyarrhythmia detector 332, a therapy output circuit 354, a therapy controller 356, a duration controller 334, a hemodynamic sensor 336, and a hemodynamic performance analyzer 338.

Sensing circuit 350 senses at least one cardiac signal, such as an atrial electrogram or a ventricular electrogram, using electrodes such as those illustrated in FIG. 1. Rate detector 352 detects a heart rate from the cardiac signal. Tachyarrhythmia detector 332 detects a tachyarrhythmia using the heart rate. In one embodiment, tachyarrhythmia detector 332 indicates that the tachyarrhythmia is detected if the heart rate falls into a tachyarrhythmia detection rate zone, such as a VT detection rate zone specified by a threshold heart rate above which a detection of VT is indicated. In one embodiment, tachyarrhythmia detector 332 includes a tachyarrhythmia classifier 358 that classifies each detected tachyarrhythmia. For example, if the detection of VT is indicated based in the heart rate, tachyarrhythmia classifier 358 confirms the detection of VT by classifying the detected tachyarrhythmia as one of VT and SVT. Therapy output circuit 354 delivers an anti-tachyarrhythmia therapy such as an ATP therapy or a cardioversion/defibrillation therapy. Therapy controller 356 controls the delivery of the anti-tachyarrhythmia therapy. In one embodiment, therapy controller 356 controls the delivery of the anti-tachyarrhythmia therapy based on whether the tachyarrhythmia is detected during the arrhythmia detection duration.

The SRD is discussed below in this document as a specific example of the arrhythmia detection duration. Tachyarrhythmia detector 332 detects the tachyarrhythmia during the SRD. In one embodiment, a tachyarrhythmia is detected by tachyarrhythmia detector 332 when the heart rate falls within the VT detection rate zone and classified as an SVT by tachyarrhythmia classifier 358. Therapy controller 356 does not initiate a delivery of the anti-tachyarrhythmia therapy in response to the classification of SVT. However, as a "safety net", the SRD is started following the classification of SVT. If the tachyarrhythmia sustains (i.e., the heart rate remains within the VT detection rate zone), and the rhythm continues to satisfy the detection criteria for withholding the ventricular therapy (for example, the ventricular rate does not exceed the atrial rate by at least 10 beats per minute, or ventricular rate is stable), therapy controller 356 initiates the delivery of the anti-tachyarrhythmia therapy when the SRD expires. If the tachyarrhythmia does not sustain during the SRD, or if the detection criteria for withholding the ventricular therapy are no longer satisfied before the scheduled expiration of the SRD, the SRD is terminated before it expires, and therapy controller 356 withholds the delivery of the anti-tachyarrhythmia therapy.

Duration controller 334 is a specific embodiment of duration controller 234 and controls the SRD. Duration controller 334 includes a duration timer 340 and a duration adjuster 342. Duration timer 340 is a specific embodiment of duration timer 240 and times the SRD. In one embodiment, duration timer 340 starts the SRD in response to the detection and classification of a predetermined-type tachyarrhythmia such as SVT. When being started, the SRD is set to a base value. When tachyarrhythmia detector 332 stops indicating that the tachyarrhythmia is detected during the SRD, duration timer 340 terminates the SRD. Therapy controller 356 withholds the delivery of the anti-tachyarrhythmia therapy if the SRD is terminated before expiring.

Duration adjuster 342 is a specific embodiment of duration adjuster 242 and adjusts the SRD. In one embodiment, as illustrated in FIG. 3, duration adjuster 342 includes a duration initialization module 344, a duration update module 346, and a dynamic duration adjustment module 348. In other embodiments, duration adjuster 342 includes any one or more of duration initialization module 344, duration update module 346, and dynamic duration adjustment module 348. If as a result of adjustment by duration adjuster 342, the SRD exceeds a specified maximum value, the SRD expires at the specified maximum value, causing therapy controller 356 to initiate the delivery of the anti-tachyarrhythmia therapy.

Figure 5:
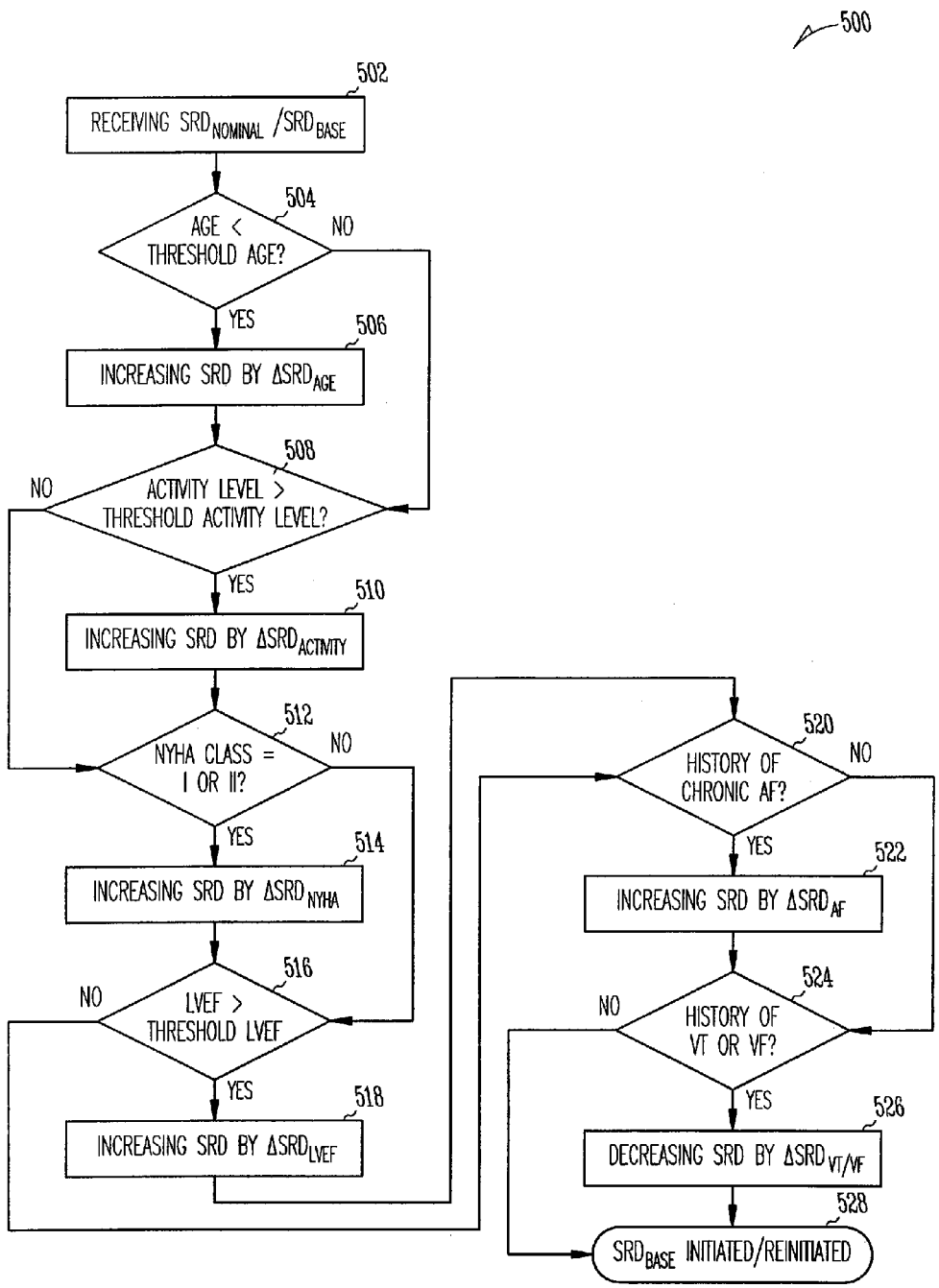
FIG. 5 is a flow chart illustrating an embodiment of a method for initializing the SRD.

Duration initialization module 344 is a specific embodiment of duration initialization module 244 and determines an initial value using the one or more indication parameters and sets the base value of the SRD to the initial value. In one embodiment, duration initialization module 344 reinitializes the base value of the SRD when the value of at least one of the one or more indication parameters has changed substantially, such as by a specified amount. In one embodiment, duration initialization module 344 calculates the initial value as a function of one or more of the nominal or current base value of the SRD, age, a physical activity level parameter, New York Heart Association (NYHA) classification, left ventricular ejection fraction (LVEF), history of chronic atrial fibrillation (AF), and history of ventricular tachycardia (VT) or ventricular fibrillation (VF). An example of a method for initializing the base value of the SRD by duration initialization module 344 is illustrated in FIG. 5 and discussed below.

Figure 6:
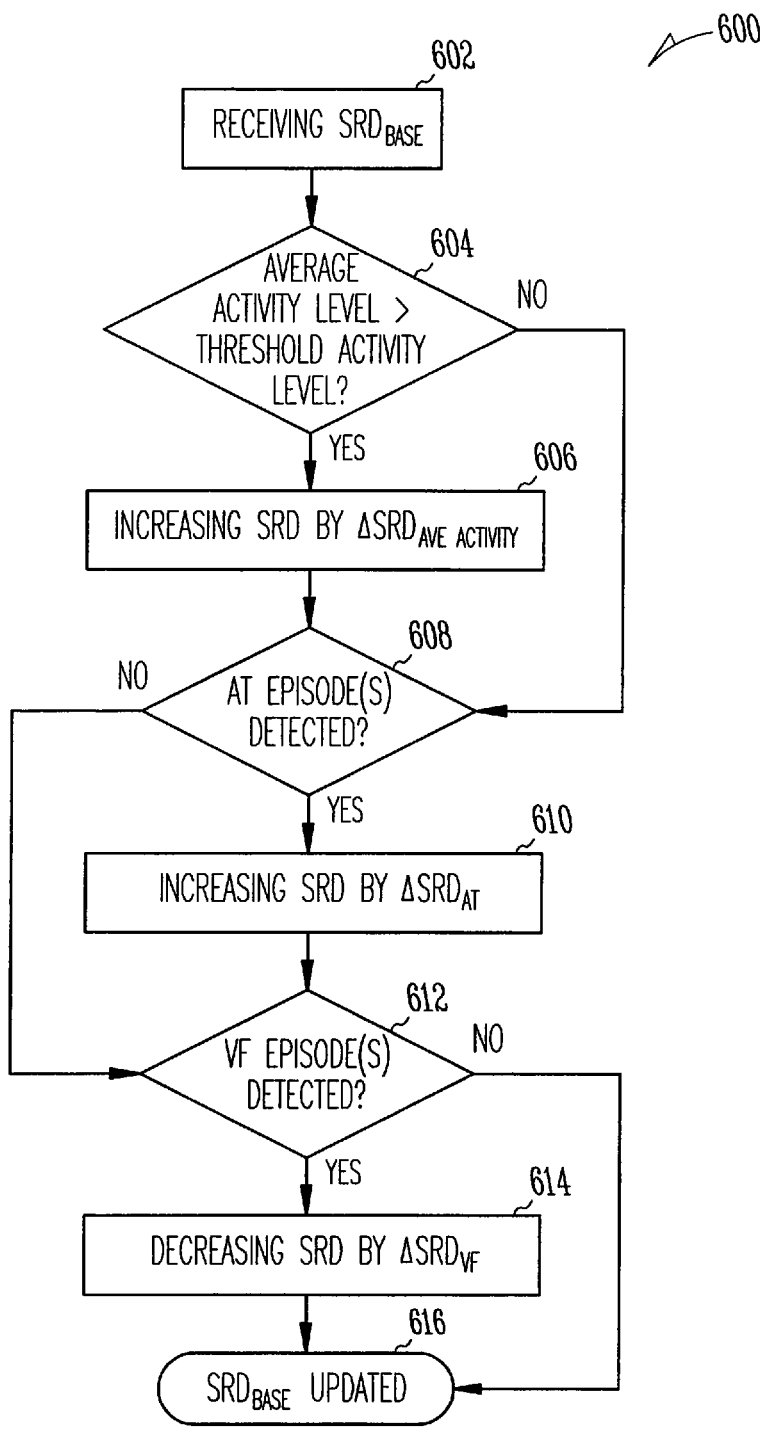
FIG. 6 is a flow chart illustrating an embodiment of a method for updating the SRD.

Duration update module 346 is a specific embodiment of duration update module 246 and determines an updated value using the one or more trend parameters and sets the base value of the SRD to the updated value. In one embodiment, duration update module 346 updates the base value of the SRD according to a predetermined schedule, such as on an approximately periodic basis. In one embodiment, duration update module 346 calculates the updated value as a function of one or more of the current base value of the SRD, an average physical activity level during a recent period, a number of AT episodes (including episodes with a fast sensed atrial rate and a slow sensed ventricular rate) detected during the recent period, and a number of VF episodes (including episodes with heart rate in a VF detection zone defined by at least one threshold heart rate) detected during the recent period. In one embodiment, the recent period is a specified length of time, such as approximately a month, before the base value of the SRD is updated. In another embodiment, the recent period is the time period between two consecutive updates of the base value of the SRD. An example of a method for updating the base value of the SRD performed by duration update module 346 is illustrated in FIG. 6 and discussed below.

Dynamic duration adjustment module 348 is a specific embodiment of dynamic duration adjustment module 248 and dynamically adjusts the SRD while the tachyarrhythmia sustains during the SRD. Hemodynamic sensor 336 senses a signal indicative of hemodynamic performance. Hemodynamic performance analyzer 338 produces a hemodynamic stability parameter. Dynamic duration adjustment module 348 calculates an adjusted value of the SRD using the hemodynamic stability parameter and sets the current value of the SRD to the adjusted value when a duration adjustment flag is set. Dynamic duration adjustment module 348 includes a duration adjustment timer 360 that controls the timing for setting the duration adjustment flag.

Hemodynamic sensor 336 is a specific embodiment of hemodynamic sensor 236 and senses the signal indicative of hemodynamic performance. Hemodynamic performance analyzer 338 is a specific embodiment of hemodynamic performance analyzer 238 and produces the hemodynamic stability parameter. In one embodiment, hemodynamic sensor 336 includes a pressure sensor that senses a blood pressure signal, and hemodynamic performance analyzer 338 detects a pulse pressure from the blood pressure signal and produces a hemodynamic stability parameter indicative of the change in the pulse pressure. The pulse pressure is the difference between the systolic pressure and the diastolic pressure. In a specific embodiment, hemodynamic sensor 336 includes a pulmonary artery pressure (PAP) sensor that senses a PAP signal, and hemodynamic performance analyzer 338 detects a pulmonary artery pulse pressure from the PAP signal and produces a hemodynamic stability parameter indicative of the change in the pulmonary artery pulse pressure. In another embodiment, hemodynamic sensor 336 includes a impedance sensor that senses a transthoracic impedance signal, and hemodynamic performance analyzer 338 detects a stroke impedance from the transthoracic impedance signal and produces a hemodynamic stability parameter indicative of the change in the stroke impedance. The stroke impedance is the peak-to-peak amplitude of the transthoracic impedance signal.

When the SRD is started with its base value in response to the detection of a predetermined-type tachyarrhythmia such as SVT, duration adjustment timer 360 calculates a duration adjustment interval as a function of the base value of the SRD and starts the duration adjustment interval. In one embodiment, the duration adjustment interval is between approximately 20% and 80% of the base value of the SRD, with approximately 50% of the base value of the SRD being a specific example. Duration adjustment timer 360 sets the duration adjustment flag when the duration adjustment interval expires. Then, duration adjustment timer 360 recalculates the duration adjustment interval as a function of the time interval between the duration adjustment flag is set and the expiration of the adjusted SRD and restarts the duration adjustment interval, unless the time interval between the duration adjustment flag is set and the expiration of the adjusted SRD exceeds a predetermined minimum time interval. In one embodiment, the recalculated duration adjustment interval is between approximately 20% and 80% of the time interval between the duration adjustment flag is set and the expiration of the adjusted SRD, with approximately 50% of the time interval between the duration adjustment flag is set and the expiration of the adjusted SRD being a specific example. The minimum time interval is required for producing the hemodynamic stability interval.

Figure 7:
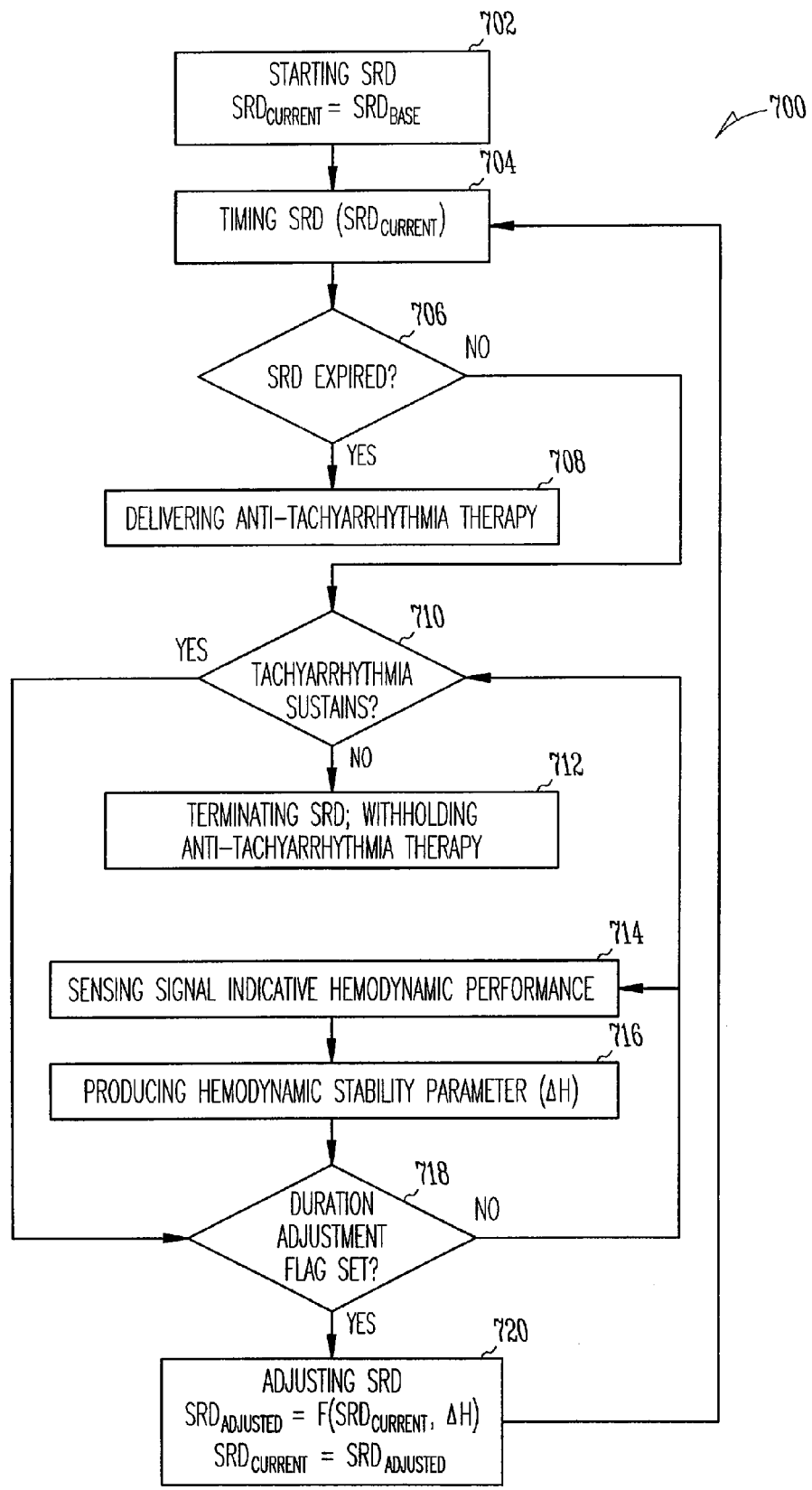
FIG. 7 is a flow chart illustrating an embodiment of a method for dynamically adjusting the SRD using a hemodynamic signal.

Dynamic duration adjustment module 348 lengthens the SRD if the hemodynamic stability parameter indicates a more stable hemodynamic performance (does not exceed a stability threshold) and shortens the SRD if the hemodynamic stability parameter indicates a less stable hemodynamic performance (exceeds the stability threshold). An example of a method for dynamically adjusting the SRD performed by dynamic duration adjustment module 348 is illustrated in FIG. 7 and discussed below.

Figure 8:
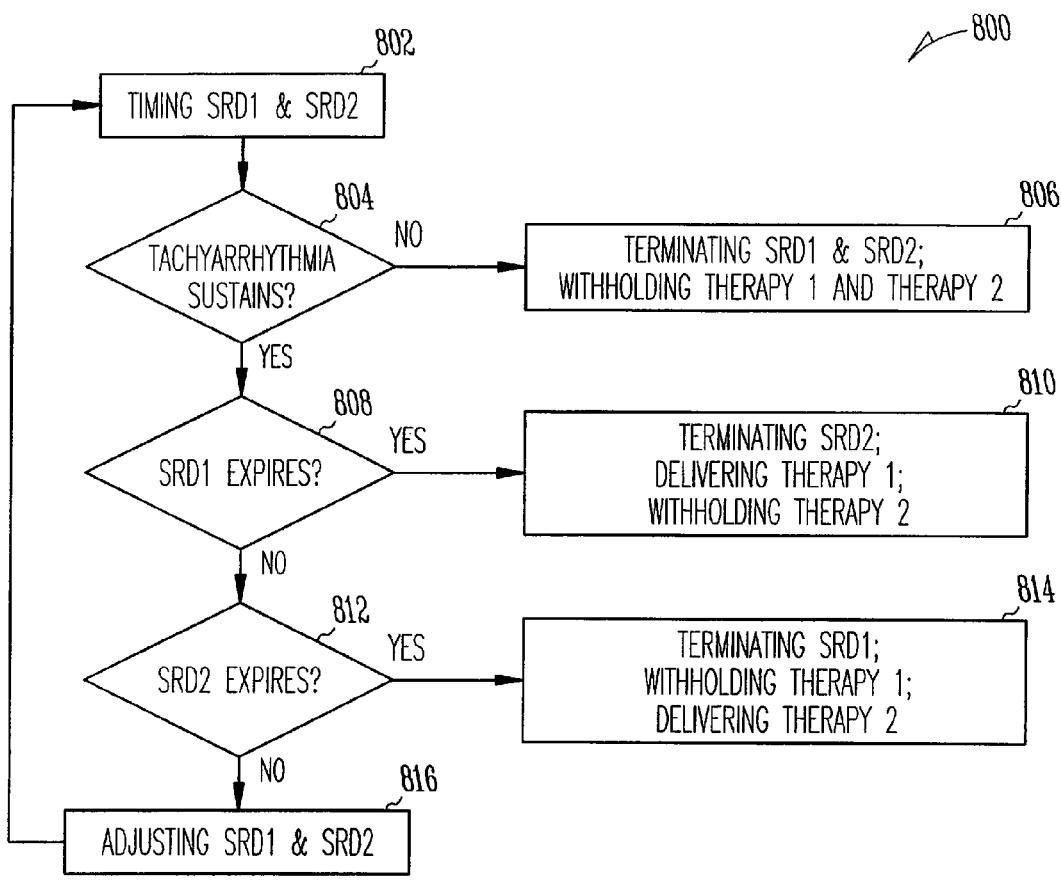
FIG. 8 is a flow chart illustrating an embodiment of a method for controlling two anti-tachyarrhythmia therapies using two adjustable SRDs.

In one embodiment, therapy output circuit 354 delivers a first type anti-tachyarrhythmia therapy and a second type anti-tachyarrhythmia therapy, and therapy controller 356 controls the delivery of the first and second type anti-tachyarrhythmia therapies. In a specific embodiment, the first type anti-tachyarrhythmia therapy is an ATP therapy, and the second type anti-tachyarrhythmia therapy is a cardioversion/defibrillation shock therapy. Duration controller 334 controls a first SRD associated with the first type anti-tachyarrhythmia therapy and a second SRD associated with the second type anti-tachyarrhythmia therapy. Duration adjuster 342 sets and adjusts the first SRD and the second SRD independently. An example of controlling two tachyarrhythmia therapies using two SRDs performed by system 320 is illustrated in FIG. 8 and discussed below.

Figure 4:
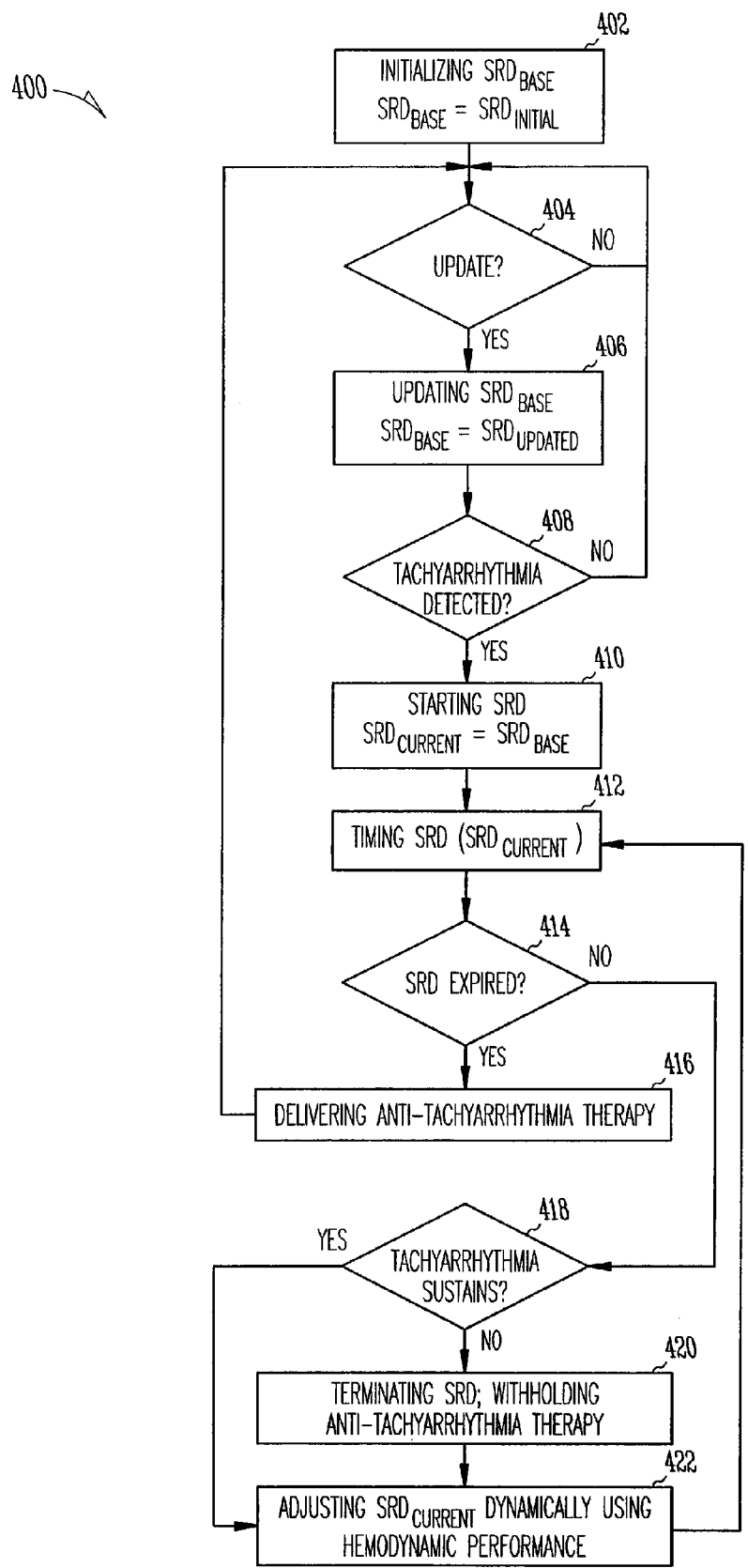
FIG. 4 is a flow chart illustrating an embodiment of a method for controlling an anti-tachyarrhythmia therapy using a sustained rate duration (SRD).

FIG. 4 is a flow chart illustrating an embodiment of a method 400 for controlling an anti-tachyarrhythmia therapy using the SRD. In one embodiment, method 400 is performed by anti-tachyarrhythmia system 320.

The base value of the SRD ($SRD_{BASE}$) is initialized by being set to an initial value ($SRD_{INITIAL}$) at 402. The initial value is automatically determined using one or more indication parameters related to an indication for the anti-tachyarrhythmia therapy. The one or more indication parameters are from a patient's medical records. When a tachyarrhythmic heart rate is being detected in a patient, the one or more indication parameters each indicate, to a certain extent, the likeliness that the patient is experiencing a tachyarrhythmia of a type that is treatable by the anti-tachyarrhythmia therapy. A specific example for initializing the $SRD_{BASE}$ is discussed below with reference to FIG. 5.

When the $SRD_{BASE}$ is to be updated at 404, the $SRD_{BASE}$ is set to an updated value ($SRD_{UPDATED}$) at 406. In one embodiment, the $SRD_{BASE}$ is updated according to a predetermined schedule. In another embodiment, the $SRD_{BASE}$ is updated on an approximately periodic basis, such as on an approximately monthly basis. In one embodiment, the $SRD_{BASE}$ is updated when deemed necessary or appropriate by a physician or other caregiver. A specific example for updating the $SRD_{BASE}$ is discussed below with reference to FIG. 6.

If a predetermined-type tachyarrhythmia is detected at 408, the SRD is started, with its current value ($SRD_{CURRENT}$) set to the $SRD_{BASE}$, at 410. The predetermined-type tachyarrhythmia is detected when a tachyarrhythmia is detected using the heart rate and classified to be the predetermined-type using a cardiac signal morphology or other cardiac signal characteristics. In one embodiment, the predetermined-type tachyarrhythmia is an SVT, which is detected when the heart rate falls within the VT detection rate zone and classified as SVT at 408. The SRD is timed at 412, with its value being the $SRD_{CURRENT}$.

If the SRD expires at 414, the anti-tachyarrhythmia therapy is delivered at 416. This concludes the response to the detection of the predetermined-type tachyarrhythmia. The tachyarrhythmia is detected throughout the SRD using the heart rate to determine whether the tachyarrhythmia (i.e., the fast heart rate) sustains. If the SRD does not expire at 414, but the tachyarrhythmia does not sustain at 418, the SRD is terminated, and the delivery of the anti-tachyarrhythmia therapy is withheld at 420. This also concludes the response to the detection of the predetermined-type tachyarrhythmia. If the SRD does not expire at 414, and the tachyarrhythmia sustains at 418, the $SRD_{CURRENT}$ is dynamically adjusted using the patient's hemodynamic performance at 422. A specific example for dynamically adjusting the $SRD_{CURRENT}$ using hemodynamic performance is discussed below with reference to FIG. 7. The SRD continues to be timed at 412, with the adjusted $SRD_{CURRENT}$. Method 400 continues to be performed until the anti-tachyarrhythmia therapy is delivered at 416 or the SRD is terminated at 420.

FIG. 5 is a flow chart illustrating an embodiment of a method 500 for initializing or reinitializing the SRD. In one embodiment, method 500 is performed by duration initialization module 344.

A nominal value for the SRD ($SRD_{NOMINAL}$) or a current $SRD_{BASE}$ is received at 502. Method 500 is performed to initialize a CRM system for its first use with a patient, and the $SRD_{NOMINAL}$ is the manufacturer-programmed value of the SRD. In one embodiment, method 500 is also performed to reinitialize the current $SRD_{BASE}$, such as when the value of at least one indication parameter used to determine the $SRD_{INITIAL}$ has changed substantially, such as by at least a specified amount. The SRD is initialized or reinitialized by increasing or decreasing the received $SRD_{NOMINAL}$ or $SRD_{BASE}$ based on the patient's indication parameters.

As illustrated in FIG. 5, the indication parameters used in method 500 include age, physical activity level, New York Heart Association (NYHA) classification, left ventricular ejection fraction (LVEF), history of chronic atrial fibrillation (AF), and history of ventricular tachycardia (VT) or ventricular fibrillation (VF). If the age is below a predetermined threshold age at 504, the SRD is increased by an amount (such as a percentage of the received $SRD_{NOMINAL}$ or $SRD_{BASE}$) associated with the age ($\Delta SRD_{AGE}$) at 506. If a physical activity level parameter exceeds a predetermined threshold activity level at 508, the SRD is increased by an amount (such as a percentage of the received $SRD_{NOMINAL}$ or $SRD_{BASE}$) associated with the physical activity level ($\Delta SRD_{ACTIVITY}$) at 510. If the NYHA classification is class I or II at 512, the SRD is increased by an amount (such as a percentage of the received $SRD_{NOMINAL}$ or $SRD_{BASE}$) associated with the NYHA classification ($\Delta SRD_{NYHA}$) at 514. If the LVEF exceeds a predetermined threshold LVEF, such as approximately 30%, at 516, the SRD is increased by an amount (such as a percentage of the received $SRD_{NOMINAL}$ or $SRD_{BASE}$) associated with the LVEF ($\Delta SRD_{LVEF}$) at 518. If the history of chronic AF is indicated (the patient has suffered AF) at 520, the SRD is increased by an amount (such as a percentage of the received $SRD_{NOMINAL}$ or $SRD_{BASE}$) associated with the history of chronic AF ($\Delta SRD_{AF}$) at 522. If the history of VT or VF is indicated (the patient has suffered VT/VF) at 524, the SRD is decreased by an amount (such as a percentage of the received $SRD_{NOMINAL}$ or $SRD_{BASE}$) associated with the history of VT or VF ($\Delta SRD_{VT/VF}$) at 526. The $SRD_{BASE}$ is initialized or reinitiated at 528, as the result of performing method 500.

In one embodiment, the thresholds or other criteria related to the indication parameters are adjusted periodically or as needed. For example, the patient's conditions after being treated may suggest the need to modify the thresholds or other criteria for a better performance in therapy control, and the progress in the understanding of the patient's cardiac conditions and treatments may also suggest such a need.

FIG. 6 is a flow chart illustrating an embodiment of a method 600 for updating the SRD using the patient's recent conditions and trends. In one embodiment, method 600 is performed by duration update module 346.

A current $SRD_{BASE}$ is received at 602. The SRD is updated by increasing or decreasing the received current $SRD_{BASE}$ using the patient's trend parameters.

As illustrated in FIG. 6, the indication parameters used in method 500 include average physical activity level, number of occurrence of AT episodes (including episodes with a fast sensed atrial rate and a slow sensed ventricular rate), and number of occurrence of VF episodes (including episodes with heart rate in a VF detection zone defined by at least one threshold heart rate). If the average physical activity level during a recent period exceeds predetermined threshold activity level at 604, the SRD is increased by an amount (such as a percentage of the received current $SRD_{BASE}$) associated with the average physical activity level ($\Delta SRD_{AVE\ ACTIVITY}$) at 606. If at least one AT episode is detected during the recent period at 608, the SRD is increased by an amount (such as a percentage of the received current $SRD_{BASE}$) associated with the number of AT episodes detected ($\Delta SRD_{AT}$) at 610. If at least one VF episode is detected during the recent period at 612, the SRD is decreased by an amount (such as a percentage of the received current $SRD_{BASE}$) associated with the number of VF episodes detected ($\Delta SRD_{AT}$) at 614. The received current $SRD_{BASE}$ is updated at 616, as the result of performing method 600.

In one embodiment, the recent period is a specified length of time, such as approximately a month, that precedes each performance of method 600. In another embodiment, the recent period is the time period between two consecutive performances of method 600. In one embodiment, the thresholds or other criteria related to the trend parameters are adjusted periodically or as needed.

FIG. 7 is a flow chart illustrating an embodiment of a method 700 for dynamically adjusting the SRD using a hemodynamic signal. In one embodiment, method 700 is performed by dynamic duration adjustment module 348. The SRD is dynamically adjusted after being started in response to the detection of a predetermined-type tachyarrhythmia such as SVT.

The SRD is started, with the $SRD_{CURRENT}$ set to the $SRD_{BASE}$, at 702, and is timed at 704. If the SRD expires at 706, an anti-tachyarrhythmia therapy is delivered at 708. This concludes the response to the detection of the predetermined-type tachyarrhythmia. The tachyarrhythmia is detected throughout the SRD using the heart rate to determine whether the tachyarrhythmia (i.e., the fast heart rate) sustains. If the SRD does not expire at 706, but the tachyarrhythmia does not sustain at 710, the SRD is terminated, and the delivery of the anti-tachyarrhythmia therapy is withheld at 712. This also concludes the response to the detection of the predetermined-type tachyarrhythmia. If the SRD does not expire at 706, and the tachyarrhythmia sustains at 710, the $SRD_{CURRENT}$ is dynamically adjusted using the patient's hemodynamic performance at 720, if a duration adjustment flag is set at 718. The duration adjustment flag is set each time when a duration adjustment interval expires. The first duration adjustment interval is calculated as a function of the $SRD_{BASE}$ and started when the SRD is started. After the duration adjustment flag is set, the next duration adjustment interval is calculated as a function of the time interval between the duration adjustment flag is set and the expiration of the $SRD_{CURRENT}$ and started when the duration adjustment flag is set. This continues as long as the SRD has not expired, the tachyarrhythmia sustains, until the time interval between the duration adjustment flag is set and the expiration of the SRD is below a predetermined minimum time interval (i.e., until the next duration adjustment interval would be too short).

To dynamically adjust the $SRD_{CURRENT}$, a signal indicative of hemodynamic performance is sensed at 714. A hemodynamic stability parameter ($\Delta H$) is produced at 716. In one embodiment, the signal indicative of hemodynamic performance is a blood pressure signal, and the hemodynamic stability parameter ($\Delta H$) is indicative of the change in the pulse pressure. In a specific embodiment, the signal indicative of hemodynamic performance is a PAP signal, and the hemodynamic stability parameter ($\Delta H$) is indicative of the change in the pulmonary artery pulse pressure. In another embodiment, the signal indicative of hemodynamic performance is a transthoracic impedance signal, and the hemodynamic stability parameter ($\Delta H$) is indicative of a change in the stroke impedance. In one embodiment, the signal indicative of hemodynamic performance is sensed by hemodynamic sensor 336, and the hemodynamic stability parameter ($\Delta H$) is produced by hemodynamic performance analyzer 338.

An adjusted value ($SRD_{ADJUSTED}$) is computed as a function of the $SRD_{CURRENT}$ and the $\Delta H$ (i.e., $SRD_{UPDATED}$=f ($SRD_{CURRENT}$, $\Delta H$)), and the $SRD_{CURRENT}$ is set to the $SRD_{ADJUSTED}$, at 720. In one embodiment, the $SRD_{ADJUSTED}$ is computed by adding a duration change ($\Delta SRD$) to the $SRD_{CURRENT}$ (i.e., $SRD_{ADJUSTED}$=$SRD_{CURRENT}$+$\Delta SRD$). The $\Delta SRD$ is the duration change being a predetermined function of the $\Delta H$ ($\Delta SRD$=f($\Delta H$)) and can be a positive or negative value, depending on the hemodynamic stability indicated by the $\Delta H$. In one embodiment, if the $\Delta H$ exceeds a stability threshold (and therefore considered unstable), the SRD is lengthened by a time interval X (i.e., $SRD_{ADJUSTED}$=$SRD_{CURRENT}$+X), and if the $\Delta H$ does not exceed the stability threshold (and therefore considered stable), the SRD is shortened by a time interval Y (i.e., $SRD_{ADJUSTED}$=$SRD_{CURRENT}$−Y). In one embodiment, X and Y are predetermined time intervals. In another embodiment, X and Y are each dynamically computed as a function of the $\Delta H$.

The SRD$_{CURRENT}$ is dynamically adjusted as long as the SRD has not expired, the tachyarrhythmia sustains, and the duration adjustment flag is set. Method 700 continues to be performed until the anti-tachyarrhythmia therapy is delivered at 708 or the SRD is terminated at 712.

FIG. 8 is a flow chart illustrating an embodiment of a method 800 for controlling two anti-tachyarrhythmia therapies using two SRDs. In one embodiment, method 800 is performed by anti-tachyarrhythmia system 320.

A first SRD (SRD1) and a second SRD (SRD2) are timed at 802. The SRD1 is associated with a first type anti-tachyarrhythmia therapy (therapy 1). The SRD2 is associated with a second type anti-tachyarrhythmia therapy (therapy 2). The values of the SRD1 and SRD2 are each independently initialized, updated, and/or dynamically adjusted according to one or more of the methods discussed above. In response to the detection of a predetermined type tachyarrhythmia, such as SVT, the SRD1 and the SRD2 are started simultaneously.

If the tachyarrhythmia does not sustain at 804, the SRD1 and SRD2 are both terminated, and the therapy 1 and therapy 2 are both withheld, at 806. If the tachyarrhythmia sustains at 804, and the SRD1 expires at 808 (before the SRD2 would expire), then the SRD2 is terminated, the therapy 1 is delivered, and the therapy 2 is withheld, at 810. If the tachyarrhythmia sustains at 804, and the SRD2 expires at 812 (before the SRD1 would expire), then the SRD1 is terminated, the therapy 1 is withheld, and the therapy 2 is delivered, at 814. If tachyarrhythmia sustains, and none of the SRD1 and SRD2 expires, the SRD1 and SRD2 are dynamically adjusted at 816 and continue to be timed at 802. The SRD1 and SRD2 are each independently adjusted by performing method 700.

The SRD1 and SRD2 are each dynamically adjusted as long as neither the SRD1 nor the SRD2 has expired, the tachyarrhythmia sustains, and its duration adjustment flag is set. Method 800 continues to be performed until the SRD1 and SRD2 are terminated at 806, the therapy 1 is delivered at 810, or the therapy 2 is delivered at 814. In one embodiment, the therapy 1 is an ATP therapy, and the therapy 2 is a cardioversion/defibrillation shock therapy. The SRD1 and SRD2 are initialized with base values promoting the use of ATP therapy while ensuring patient safety by preventing a prolonged delay before delivering the cardioversion/defibrillation shock therapy when necessary.

It is to be understood that the above detailed description is intended to be illustrative, and not restrictive. For example, the arrhythmia detection duration such as the SRD may be initialized, updated, and/or dynamically adjusted using any signals or parameters known to affect hemodynamic performance and/or indicate the need for an anti-tachyarrhythmia therapy. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management system, comprising:
a hemodynamic sensor adapted to sense a signal indicative of hemodynamic performance;
a tachyarrhythmia detector adapted to detect a tachyarrhythmia and determine whether the detected tachyarrhythmia sustains during an arrhythmia detection duration; and
a duration controller coupled to the tachyarrhythmia detector, the duration controller including:
a duration timer adapted to initiate and time the arrhythmia detection duration in response to a detection of the tachyarrhythmia; and
a duration adjuster coupled to the duration timer, the duration adjuster including:
a duration initialization module adapted to automatically determine an initial value using one or more indication parameters each indicating likeliness of occurrence of a tachyarrhythmia and set a base value of the arrhythmia detection duration to the initial value, the one or more indication parameters including patient demographics; and
a dynamic duration adjustment module adapted to dynamically adjust the arrhythmia detection duration using the signal indicative of hemodynamic performance during the arrhythmia detection duration.

2. The system of claim 1, wherein the hemodynamic sensor comprises a pressure sensor adapted to sense a pulmonary artery pressure.

3. The system of claim 1, wherein the hemodynamic sensor comprises an impedance sensor adapted to sense a transthoracic impedance.

4. The system of claim 1, wherein the duration adjuster comprises:
the duration initialization module; and
a duration update module adapted to determine an updated value using one or more trend parameters related to a recent trend of a medical condition and to set the base value of the arrhythmia detection duration to the updated value.

5. The system of claim 4, wherein the duration initialization module is adapted to reinitialize the base value of the arrhythmia detection duration in response to a change of a value of at least one of the one or more indication parameters by at least a specified amount.

6. The system of claim 1, wherein the arrhythmia detection duration is a sustained rate duration (SRD) during which whether the detected tachyarrhythmia sustains is determined, and the duration timer is adapted to start the SRD in response to the detected tachyarrhythmia being classified as a supraventricular tachyarrhythmia, and further comprising:
a therapy output circuit adapted to deliver the anti-tachyarrhythmia therapy; and
a therapy controller coupled to the therapy output circuit, the therapy controller adapted to initiate a delivery of the anti-tachyarrhythmia therapy in response to an expiration of the SRD and to withhold the delivery of the anti-tachyarrhythmia therapy if the SRD is terminated before the expiration.

7. A method for operating a cardiac rhythm management system, the method comprising:
sensing a signal indicative of hemodynamic performance;
initiating and timing an arrhythmia detection duration in response to a detected tachyarrhythmia;
determining whether the detected tachyarrhythmia sustains during the arrhythmia detection duration; and
adjusting the arrhythmia detection duration, including initializing the arrhythmia detection duration automatically using one or more indication parameters each indicating likeliness of occurrence of a tachyarrhythmia and adjusting the arrhythmia detection duration dynamically using the signal indicative of hemodynamic performance during the arrhythmia detection duration, the one or more indication parameters including patient demographics.

8. The method of claim 7, wherein adjusting the arrhythmia detection duration comprises:
determining an initial value using the one or more indication parameters; and setting a base value of the arrhythmia detection duration to the initial value.

9. The method of claim 8, further comprising:
determining an updated value using one or more trend parameters related to a recent trend of a medical condition; and
setting the base value of the arrhythmia detection duration to the updated value.

10. The method of claim 8, further comprising reinitializing the base value of the arrhythmia detection duration in response to a change of a value of at least one of the one or more indication parameters by at least a specified amount.

11. The method of claim 7, wherein the arrhythmia detection duration is a sustained rate duration (SRD) during which whether the detected tachyarrhythmia sustains is determined, and further comprising:
starting the SRD in response to the detected tachyarrhythmia being classified as a supraventricular arrhythmia;
initiating a delivery of the anti-tachyarrhythmia therapy in response to an expiration of the SRD; and
withholding the delivery of the anti-tachyarrhythmia therapy if the SRD is terminated before expiring.

12. A cardiac rhythm management system, the system comprising:
a hemodynamic sensor adapted to sense a signal indicative of hemodynamic performance;
a tachyarrhythmia detector adapted to detect a tachyarrhythmia, classify the detected tachyarrhythmia as one of a supraventricular tachyarrhythmia or a ventricular tachyarrhythmia, and in response to the detected tachyarrhythmia being classified as the supraventricular tachyarrhythmia, determine whether the supraventricular tachyarrhythmia sustains during a sustained rate duration (SRD);
a therapy output circuit adapted to deliver an anti-tachyarrhythmia therapy;
a therapy controller coupled to the therapy output circuit, the therapy controller adapted to initiate a delivery of the anti-tachyarrhythmia therapy in response to an expiration of the SRD and to withhold the delivery of the anti-tachyarrhythmia therapy if the SRD is terminated before the expiration; and
a duration controller coupled to the tachyarrhythmia detector, the duration controller including:
a duration timer adapted to start and time the SRD in response to the detected tachyarrhythmia being classified as the supraventricular tachyarrhythmia, and not to start and time the SRD in response to the detected tachyarrhythmia being classified as the ventricular tachyarrhythmia; and
a duration adjuster coupled to the duration timer, the duration adjuster including a dynamic duration adjustment module adapted to dynamically adjust the SRD using the signal indicative of hemodynamic performance during the SRD.

13. The system of claim 12, wherein the duration timer is adapted to terminate the SRD in response to a determination by the tachyarrhythmia detector that the supraventricular tachyarrhythmia no longer sustains during the SRD.

14. The system of claim 12, further comprising a hemodynamic performance analyzer coupled to the hemodynamic sensor, the hemodynamic performance analyzer adapted to produce a hemodynamic stability parameter, and wherein the dynamic duration adjustment module is adapted to compute an adjusted value of the SRD as a function of the hemodynamic stability parameter and a current value of the SRD and to set the current value of the SRD to the adjusted value of the SRD in response to a duration adjustment flag.

15. The system of claim 14, wherein duration adjuster comprises a duration adjustment timer adapted to:
calculate a duration adjustment interval as a function of a base value of the SRD and start the duration adjustment interval when the SRD is started;
set the duration adjustment flag in response to an expiration of the duration adjustment interval; and
recalculate the duration adjustment interval as a function of the time interval between the duration adjustment flag is set and the expiration of the SRD and restart the duration adjustment interval in response to the duration adjustment flag, if the time interval between when the duration adjustment flag is set and the expiration of the SRD exceeds a predetermined minimum time interval.

16. The system of claim 14, wherein the therapy output circuit is adapted to deliver a first type anti-tachyarrhythmia therapy and a second type anti-tachyarrhythmia therapy, the hemodynamic performance analyzer is adapted to assess a hemodynamic performance during at least a portion of the SRD, and the therapy controller is adapted to select one of the first type anti-tachyarrhythmia therapy and the second type anti-tachyarrhythmia therapy based on the assessed hemodynamic performance.

17. The system of claim 16, wherein the duration timer is adapted to start a first SRD and a second SRD simultaneously, to terminate the first SRD and the second SRD when the supraventricular tachyarrhythmia is no longer detected by the tachyarrhythmia detector during the first SRD and the second SRD, to terminate the first SRD in response to an expiration of the second SRD, and to terminate the second SRD in response to an expiration of the first SRD.

18. The system of claim 17, wherein the duration adjuster is adapted to adjust the first SRD and the second SRD independently, and therapy controller is adapted to initiate a delivery of the first therapy in response to the expiration of the first SRD if the first SRD expires before the second SRD expires, and to initiate a delivery of the second therapy in response to the expiration of the second SRD if the second SRD expires before the first SRD expires.

19. The system of claim 12, wherein the duration adjuster comprises a duration initialization module adapted to automatically determine an initial value using one or more indication parameters related to an indication for an anti-tachyarrhythmia therapy and to set a base value of the SRD to the initial value.

20. The system of claim 19, wherein the duration initialization module is adapted to compute the initial value as a function of one or more of an age, a physical activity level parameter, a New York Heart Association classification, a left ventricular ejection fraction, a history of chronic atrial fibrillation, and a history of ventricular tachycardia or ventricular fibrillation.

21. The system of claim 19, wherein the duration adjuster comprises a duration update module adapted to determine an updated value using one or more trend parameters related to a recent trend of a medical condition and to set the base value of the SRD to the updated value.

22. The system of claim 21, wherein the duration update module is adapted to compute the updated value as a function of one or more of an average physical activity level during a recent period, a number of atrial tachyarrhythmia episodes detected during the recent period, and a number of ventricular tachyarrhythmia episodes detected during the recent period.

23. A method for operating a cardiac rhythm management system, the method comprising:

sensing a signal indicative of hemodynamic performance;
detecting a tachyarrhythmia;
classifying the tachyarrhythmia as one of a supraventricular tachyarrhythmia or a ventricular tachyarrhythmia;
initiating a sustained rate duration (SRD) in response to the detected tachyarrhythmia being classified as the supraventricular tachyarrhythmia;
receiving one or more of a sensed physiologic signal and stored patient-specific information;
adjusting the SRD dynamically using the signal indicative of hemodynamic performance during the SRD;
determining whether the supraventricular tachyarrhythmia sustains during the SRD;
initiating a delivery of an anti-tachyarrhythmia therapy in response to an expiration of the SRD; and
withholding the delivery of the anti-tachyarrhythmia therapy if the SRD is terminated before expiring.

24. The method of claim 23, further comprising producing a hemodynamic stability parameter using the signal indicative of hemodynamic performance,
and wherein adjusting the SRD comprises adjusting the SRD using the hemodynamic stability parameter.

25. The method of claim 24, wherein sensing the hemodynamic signal comprises sensing a pulmonary artery pressure, and producing the hemodynamic stability parameter comprises:
detecting a pulmonary artery pulse pressure being a difference between a systolic artery pulse pressure and a diastolic artery pulse pressure; and
producing a hemodynamic stability parameter indicative of a change in the pulmonary artery pulse pressure.

26. The method of claim 24, wherein sensing the hemodynamic signal comprises sensing a transthoracic impedance, and producing the hemodynamic stability parameter comprises:
detecting a stroke impedance being the peak-to-peak amplitude of the transthoracic impedance signal; and
producing a hemodynamic stability parameter indicative of a change in the stroke impedance.

27. The method of claim 24, wherein adjusting the SRD comprises:
lengthening the SRD if the hemodynamic stability parameter does not exceed a stability threshold; and
shortening the SRD if the hemodynamic stability parameter exceeds the stability threshold.

28. The method of claim 27, wherein adjusting the SRD using the signal indicative of hemodynamic performance comprises adjusting the SRD using the signal indicative of hemodynamic performance in response to a duration adjustment flag, and further comprising:
computing a duration adjustment interval as a function of a base value of the SRD and starting the duration adjustment interval when the SRD is started;
setting the duration adjustment flag in response to an expiration of the duration adjustment interval; and
recalculating the duration adjustment interval as a function of the time interval between when the duration adjustment flag is set and the expiration of the SRD and restarting the duration adjustment interval in response to the duration adjustment flag, if the time interval between the duration adjustment flag is set and the expiration of the SRD exceeds a predetermined minimum time interval.

29. The method of claim 23, further comprising terminating the SRD in response to a determination that the supraventricular tachyarrhythmia no longer sustains during the SRD.

30. The method of claim 29, further comprising:
starting a further SRD in response to the detected tachyarrhythmia being classified as the supraventricular tachyarrhythmia;
terminating the SRD in response to the determination that the supraventricular tachyarrhythmia no longer sustains during the SRD and in response to an expiration of the further SRD; and
terminating the further SRD in response to a determination that the supraventricular tachyarrhythmia no longer sustains during the further SRD and in response to an expiration of the SRD.

31. The method of claim 23, wherein adjusting the SRD comprises:
determining an initial value using one or more indication parameters related to an indication for the anti-tachyarrhythmia therapy; and
setting a base value of the SRD to the initial value.

32. The method of claim 31, wherein determining the initial value comprises calculating the initial value as a function of one or more of an age, a physical activity level parameter, a New York Heart Association (NYHA) classification, a left ventricular ejection fraction (LVEF), a history of chronic atrial fibrillation (AF), and a history of ventricular tachycardia (VT) or ventricular fibrillation (VF).

33. The method of claim 31, wherein adjusting the SRD further comprises:
determining an updated value using one or more trend parameters related to a recent trend of a medical condition; and
setting the base value of the arrhythmia detection duration to the updated value.

34. The method of claim 33, wherein determining the updated value comprises calculating the updated value as a function of one or more of an average physical activity level during a recent period, a number of atrial tachyarrhythmia episodes detected during the recent period, and a number of ventricular tachyarrhythmia episodes detected during the recent period.

* * * * *